United States Patent [19]
Jessup et al.

[11] Patent Number: 5,659,934
[45] Date of Patent: Aug. 26, 1997

[54] METHOD OF FORMING A LATERALLY EXPANDABLE TAMPON

[75] Inventors: James Lyle Jessup, Appleton; Donald Henry Paalman, Kaukauna, both of Wis.

[73] Assignee: Kimberly-Clark Worldwide, Inc., Neenah, Wis.

[21] Appl. No.: 700,599

[22] Filed: Aug. 12, 1996

[51] Int. Cl.$^6$ .................................................. A61F 13/22
[52] U.S. Cl. ........................... 28/120; 604/385.1; 604/904
[58] Field of Search ......................... 28/118, 119, 120; 604/385.1, 904, 358

[56] References Cited

U.S. PATENT DOCUMENTS

| | | | |
|---|---|---|---|
| 2,092,427 | 9/1937 | Ross | 128/285 |
| 2,264,586 | 12/1941 | Ross | 128/285 |
| 2,487,200 | 11/1949 | Trager | 128/285 |
| 2,501,972 | 3/1950 | Seidler | 128/263 |
| 2,711,173 | 6/1955 | Seidler | 128/263 |
| 2,938,519 | 5/1960 | Marco | 128/285 |
| 3,011,495 | 12/1961 | Brecht | 28/118 |
| 3,051,177 | 8/1962 | Wilson | 604/904 |
| 3,138,159 | 6/1964 | Schmidt | 128/285 |
| 3,369,544 | 2/1968 | Crockford | 128/285 |
| 3,469,286 | 9/1969 | Crockford | 28/120 |
| 3,643,661 | 2/1972 | Crockford | 128/263 |
| 3,683,915 | 8/1972 | Voss | 604/904 |
| 3,706,311 | 12/1972 | Kokx et al. | 128/285 |
| 3,749,094 | 7/1973 | Duncan | 128/285 |
| 3,762,413 | 10/1973 | Hanke | 128/285 |
| 4,018,225 | 4/1977 | Elmi | 604/904 |
| 4,212,301 | 7/1980 | Johnson | 128/285 |
| 4,266,546 | 5/1981 | Roland et al. | 128/285 |
| 4,318,407 | 3/1982 | Woon | 28/120 |
| 4,335,721 | 6/1982 | Matthews | 128/285 |
| 4,486,191 | 12/1984 | Jacob | 604/330 |
| 5,112,348 | 5/1992 | Glassman | 604/358 |
| 5,158,535 | 10/1992 | Paul et al. | 604/15 |
| 5,533,990 | 7/1996 | Yeo | 604/363 |

*Primary Examiner*—Amy B. Vanatta
*Attorney, Agent, or Firm*—Thomas J. Connelly

[57] ABSTRACT

A method of forming a tampon is disclosed wherein the tampon is useful in preventing premature leakage of body fluid from a woman's vagina, especially during her menstrual period. The method includes the steps of cutting individual absorbent members from an absorbent strip. Each absorbent member is then shaped to form an elongated absorbent having an outer periphery. A liquid-permeable cover is secured to the outer periphery of the elongated absorbent to form a softwind. The softwind has a first end and a second end. The softwind is then folded on itself such that the first and second ends are aligned adjacent to one another and the softwind contains at least two folds therebetween. The softwind is then compressed into a pledger and a withdrawal string is secured thereto to form a tampon. Alternatively, the withdrawal string can be attached to the softwind before it is compressed. The withdrawal string facilitates removal of the tampon from a woman's vagina.

20 Claims, 7 Drawing Sheets

METHOD OF FORMING A LATERALLY EXPANDABLE TAMPON

FIELD OF THE INVENTION

This invention relates to a method of forming a tampon which is capable of expanding laterally while in use to reduce leakage of body fluid. More specifically, this invention relates to a method of forming a catamenial tampon having a generally M-shaped profile which is capable of expanding laterally while in use to significantly reduce leakage of body fluid.

BACKGROUND OF THE INVENTION

Currently, there are two basic types of catemenial tampons used for feminine hygiene. The first type is a digital tampon which is designed to be inserted into a woman's vagina directly by the user's fingers. The second type is a tampon which is designed to be inserted with the aid of an applicator. Both types are usually made by folding or rolling a loosely associated strip of absorbent material into an elongated shape referred to as a "softwind". The softwind may or may not include a cover. The softwind is then radially and/or biaxially compressed into a pledget. In both types of tampons, a withdrawal string is attached to the absorbent, either before or after compression, to facilitate removal of the tampon from the user's vagina after it has absorbed a certain quantity of body fluid, such as menses, blood, etc.

It has been found that many tampons, both digital as well as those delivered by an applicator, are unable to prevent leakage of body fluid. Fluid leakage can result from a number of factors. One factor is that the tampon does not properly fit the introital region of the vagina. A second factor is that the tampon has been compressed to such an extent that it is unable to open or radially expand rapidly enough after initial insertion into a woman's vagina to absorb the body fluid which comes into contact with it. A third factor is that the tampon is not shaped correctly to intercept fluid flow through the vaginal canal. A fourth factor is that the folds and convolutions of the vagina are not all in contact with the tampon and therefore body fluid is able to bypass the tampon. A fifth factor is that the tampon does not contain a sufficient amount of absorbent material at it's insertion end to be able to completely absorb and distribute the body fluid that contacts it.

Now a method of forming a catemenial tampon has been invented. The method includes forming a tampon having a generally M-shaped profile which provides a greater amount of absorbent material at the insertion end for preventing leakage of body fluid after the tampon has been inserted into a woman's vagina.

SUMMARY OF THE INVENTION

Briefly, this invention relates to a tampon which is capable of expanding laterally while in use to significantly reduce leakage of body fluid from a woman's vagina, especially during her menstrual period. The tampon includes an absorbent and a liquid-permeable cover. The cover at least partially surrounds the absorbent and together they form an elongated softwind having a first end and a second end. The softwind is folded upon itself at two and, preferably three, spaced apart locations to form an M-shaped profile. The M-shaped profile is then compressed into an elongated pledget having an insertion end and a trailing end. The insertion end contains a greater amount of absorbent than the trailing end and has a cleft formed therein as a result of the folding. The cleft, together with the resilient characteristics of the absorbent material, facilitates the lateral expansion of the pledget immediately upon insertion of the tampon into a woman's vagina. The tampon further includes a withdrawal string which facilitates removal of the tampon from a woman's vagina.

The method of forming the tampon includes the steps of cutting individual absorbent members from an absorbent strip. Each absorbent member is then shaped to form an elongated absorbent having an outer periphery. A liquid-permeable cover is secured to the outer periphery of the elongated absorbent to form a softwind. The softwind has a first end and a second end. The softwind is then folded on itself such that the first and second ends are aligned adjacent to one another and the softwind contains at least two folds therebetween. The softwind is then compressed into a pledget and a withdrawal string is secured thereto to form a tampon. Alternatively, the withdrawal string can be attached to the softwind before it is compressed. The withdrawal string facilitates removal of the tampon from a woman's vagina.

The general object of this invention is to provide a method of forming a tampon which is capable of expanding laterally while in use to reduce leakage of body fluid. A more specific object of this invention is to provide a method of forming a catamenial tampon having a generally M-shaped profile which is capable of expanding laterally while in use to significantly reduce leakage of body fluid.

Another object of this invention is to provide a method of forming a tampon which can reduce by-pass leakage of body fluid by expanding asymmetrically to a shape which approximates the shape of the vaginal cavity.

A further object of this invention is to provide a method of forming a laterally expandable tampon which will expand upon insertion into a woman's vagina.

Still further, an object of this invention is to provide a method of forming a tampon having an insertion end and a trailing end, with the insertion end containing a greater amount of absorbent material than the trailing end so as to prevent leakage of body fluid.

Still another object of this invention is to provide a method of forming a tampon which is capable of expanding laterally and the expansion is initiated by normal movements of the body organs and muscles surrounding the vagina.

Still further, an object of this invention is to provide a method of forming a tampon which is expandable to fit the non-circular cross-sectional profile of a woman's vagina.

Other objects and advantages of the present invention will become more apparent to those skilled in the art in view of the following description and the accompanying drawings.

DETAILED DESCRIPTION OF THE PREFERRED EMBODIMENTS

Figures 1, 2:
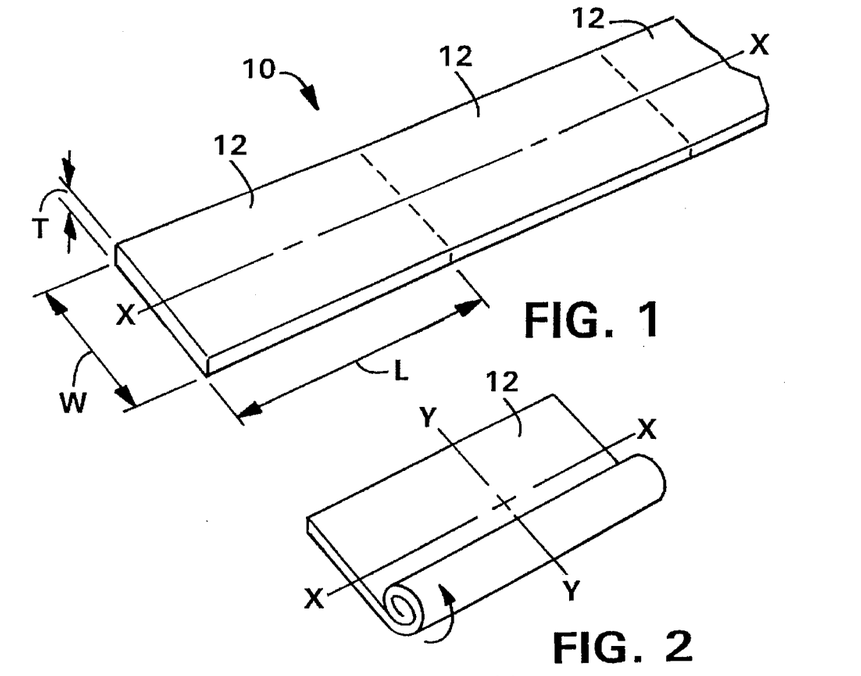
FIG. 1 is a perspective view of an elongated ribbon of absorbent material which can be cut into individual segments.
FIG. 2 is a perspective view of an individual absorbent segment being rolled up into a cylindrical profile.

Referring to FIG. 1, an elongated absorbent ribbon 10 is shown which can be cut into a plurality of individual members 12. Each of the individual members 12 can be in the form of a rectangle having a length "L", a width "W" and a thickness "T". Preferably, the length "L" will be greater than the width "W".

The absorbent ribbon 10 can be formed from absorbent fibers which are assembled into a sheet or ribbon. Alternatively, the absorbent fibers can be assembled and formed into a generally cylindrical configuration if desired. The absorbent ribbon 10 can be formed from cellulosic fibers, such as cotton and rayon. The absorbent fibers can be 100% cotton, 100% rayon, or a blend of cotton and rayon fibers. Some blends which have been tried and work well include a blend of about 15% cotton to about 85% rayon; about 70% cotton to about 30% rayon; about 60% cotton to about 40% rayon; about 25% cotton to about 75% rayon; and about 6% cotton to about 94% rayon. The particular blend of fibers can vary depending upon preference. It is also possible to add polyester or other synthetic fibers to the blend to add resilient features to the absorbent 10.

When cotton fibers are used, the cotton fibers should have a staple length of between about 5 millimeters (mm) to about 20 min. The cotton fibers should generally have a fiber size of between about 150 microns to about 280 microns. The cotton fibers can also be bleached if desired. Bleaching will make the cotton fibers whiter in appearance.

When rayon fibers are present, the rayon fibers should have a staple length of between about 20 mm to about 35 mm. The rayon fibers should have a denier of between about 2 to about 6. As defined by the "Dictionary of Fiber & Textile Technology" available from Hoechst Celanese Corporation having a mailing address of P.O. Box 32414, Charlotte, N.C. 28232 on page 42, denier is:

"the unit of fineness of yarn based on a standard of 50 milligrams (mg) for 450 meters of yarn. This is numerically equal to the weight in grams of 9,000 meters of the material. Denier is a direct numbering system in which the lower numbers represent the finer sizes and the higher numbers the coarser sizes."

The rayon fibers can have a circular, bi-lobal, a tri-lobal cross-sectional configuration, or some other cross-sectional configuration known to those skilled in the art. The bi-lobal configuration has a cross-sectional profile which looks like a dogbone while the tri-lobal configuration has a cross-sectional profile which looks like a "Y". The rayon fibers can also be bleached if desired.

The absorbent 10, when formed from an absorbent sheet or ribbon, is constructed from a blend of cotton and rayon fibers. Two processes for forming such an absorbent sheet are known as "carding" and "airlaying." Depending upon the desired absorbency one desires in the finished tampon, the basis weight of the absorbent ribbon can vary. The U.S. Food and Drug Administration (FDA) has set absorbency standards for "junior", "regular", "super" and "super-plus" size tampons. In order to meet the FDA standards for the four sizes, the absorbent sheets 10 are targeted to have basis weights of about 100 grams per square meter (gsm), 120 gsm, 170 gsm and 230 gsm, respectively. Typically, the carding process is controlled to produce an absorbent ribbon 10 having a width "W" of between about 40 mm to about 60 mm, preferably about 50 mm. The basis weight and/or the length of the absorbent can also be adjusted to form the different size tampons.

The length "L" of the individual absorbent member 12 can vary from between about 100 mm to about 200 mm. For the "regular" size tampon, a length "L" of between about 140 mm to about 150 mm is sufficient.

In FIG. 1, the individual absorbent members 12 is shown having a central longitudinal axis X—X which is in the machine direction. The central longitudinal axis X—X will be used as a reference line in some of the following figures in order to describe forming the absorbent ribbon 10 into a tampon.

Figures 3, 4:
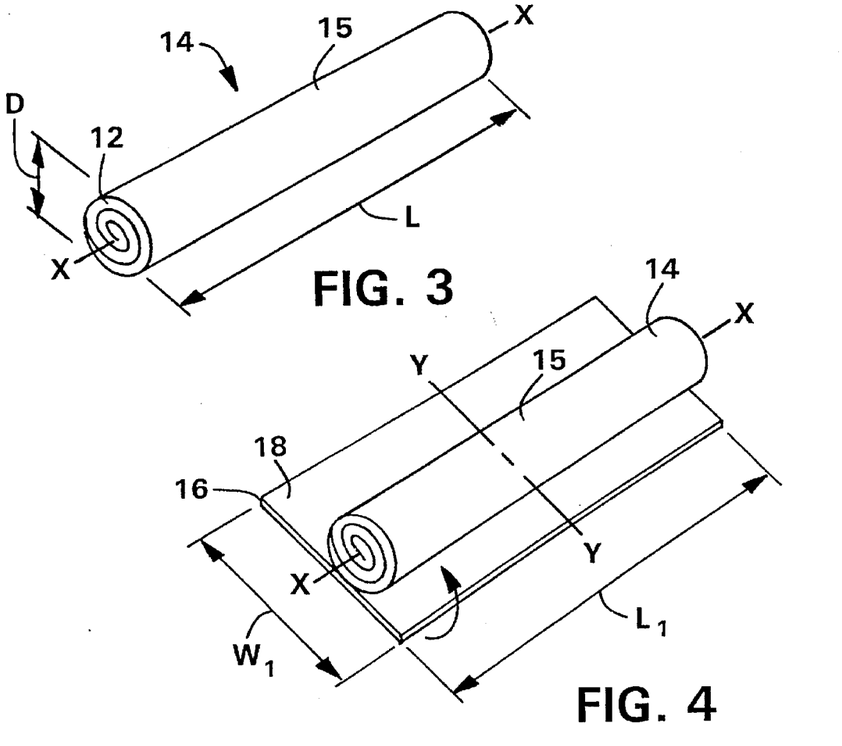
FIG. 3 is a perspective view of the individual absorbent segment having been rolled up into an elongated cylindrical shape.
FIG. 4 is a perspective view of the elongated cylindrically shaped absorbent positioned on a rectangular sheet of cover material.

Referring to FIGS. 2 and 3, an individual absorbent member 12 is shown which is rolled or folded along a central transverse axis Y—Y to form a generally elongated absorbent 14, see FIG. 3. The elongated absorbent 14 can have a cylindrical shape, a rectangular shape, an oval shape, a square shape, etc. Preferably, the absorbent 14 will have a cylindrical shape with a circular cross-section. The cross-section can have a diameter "D" which is between about 10 mm to about 20 mm. Preferably, the diameter "D" will be between about 12 mm to about 15 mm. The actual diameter "D" of the elongated absorbent 14 can vary depending upon whether it is going to be used to make a "junior", "regular", "super" or "super-plus" size tampon. The length of the elongated absorbent 14 will be approximately equal to the length of the starting individual member 12.

Figure 5:
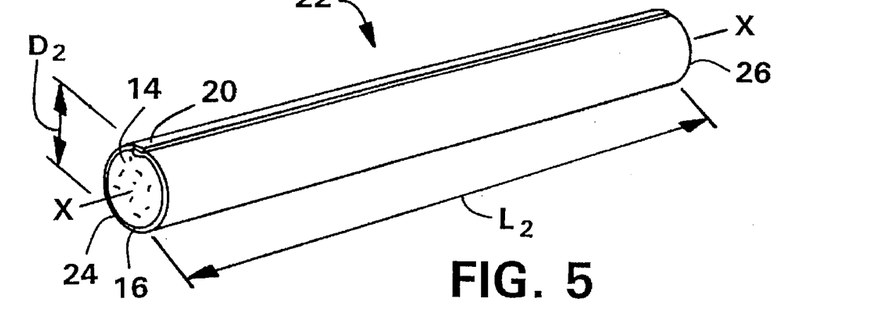
FIG. 5 is a perspective view of the absorbent rolled up with the cover material to form a "softwind."

Referring now to FIGS. 4 and 5, the elongated absorbent 14 is placed or positioned on a liquid-permeable cover 16.

The cover 16 will have a first major surface 18 and can be formed as a rectangular sheet, as shown. The cover 16 has a length $L_1$ and a width $W_1$ which are sized so that the cover 16 can wrap completely around the outer periphery of the elongated absorbent 14. Preferably, the cover 16 will have a length $L_1$ which is equal to or greater than the length L of the elongated absorbent 14 and will have a width $W_1$ which is greater than the outside periphery of the rolled absorbent 14. By so sizing the width $W_1$ of the cover 16, the cover 16 will be able to wrap completely around the outer exterior surface of the absorbent 14 and be overlapped upon itself at 20 (see FIG. 5).

The liquid-permeable cover 16 can be bonded along the entire length of the overlap area 20 by using an impulse sealer or some other type of sealing mechanism. Alternatively, the cover 16 can be spot bonded at spaced apart points along the overlap area 20, if desired. The cover 16 can be bonded to either itself and/or to the absorbent 14 using heat, pressure, heat and pressure, ultrasonics, adhesives, glue, or any other known bonding technique.

The liquid-permeable cover 16 can be formed from woven or nonwoven material having a porous substrate. Woven material includes textile fabrics which can be made from rayon, cotton, polyolefins or other synthetic yarns. The synthetics can be either staple or continuous filaments. The cover 16 can be a 0.6 ounces per square yard of polypropylene spunbond. The nonwoven materials can include spunbond, bonded carded webs and hydroentangled webs. Spunbond and bonded carded webs are commercially sold by Kimberly-Clark Corporation, having an office located at 401 North Lake Street, Neenah, Wis. 54956. Another nonwoven material which can be used as the cover 16 is formed from 100 percent polyester fibers held together by a binder. This material is known as powder-bonded-carded web (PBCW). PBCW is commercially available from HDK Industries, Inc. having an office at 304 Arcadia Drive, Greenville, S.C. 29609. The cover 16 can further be formed from an apertured thermoplastic film having either a two-dimensional or a three-dimensional thickness. Apertured thermoplastic films are available from several commercial vendors including Pantex Sri, Pantex Sud srl, Via Terracini snc, having an office at 51031 Agliana, Pistoia, Italy and Applied Extrusion Technology having a mailing address of P.O. Box 582, Middleton, Del. 19709.

The liquid-permeable cover 16 can be treated with an aqueous solution to reduce frictional drag, to enhance the tampon's wettability and to enhance the ease of insertion into and withdrawal from a woman's vagina. The cover 16 can be treated either before being rolled up with the absorbent ribbon 10 or after the cover 16 has been positioned about the exterior surface of the elongated absorbent 14. The different types of aqueous solutions which can be used are known to those skilled in the art. One particular type of aqueous solution is taught in U.S. Ser. No. 08/311,692, filed Sep. 23, 1994 and entitled "TAMPON EXHIBITING LOW FRICTIONAL DRAG". This patent application is assigned to Kimberly-Clark Corporation and is incorporated by reference and made a part hereof.

Referring again to FIG. 5, the absorbent ribbon 10 and the liquid-permeable cover 16 are rolled into a generally cylindrical-shape known as a "softwind" 22. The softwind 22 has a central longitudinal axis X—X and is an elongated member. The softwind 22 can have a shape different from the cylindrical shape if desired. The softwind 22 has a first end 24 and a second end 26. The ends 24 and 26 are spaced apart from one another. The softwind 22 can have a length $L_2$ of up to about 10 inches (about 254 mm). Preferably, the softwind 22 has a length $L_2$ of from between about 2 inches to about 8 inches (about 50 mm to about 203 mm), and most preferably, it has a length of about 6 inches (about 152 mm). When the softwind 22 has a circular cross-sectional configuration, it can have a diameter $D_2$ ranging from between about 0.5 inches (about 13 mm) to about 2 inches (about 50 mm), and preferably, will have a diameter $D_2$ of about 1 inch (about 25.4 mm). The specific diameter $D_2$ of the softwind 22 will be dictated by the type of tampon which is to be formed, such as a "junior", "regular", "super", or "super-plus" size. The softwind 22 is generally not compressed and if compressed, is not compressed a substantial amount.

Figure 6:
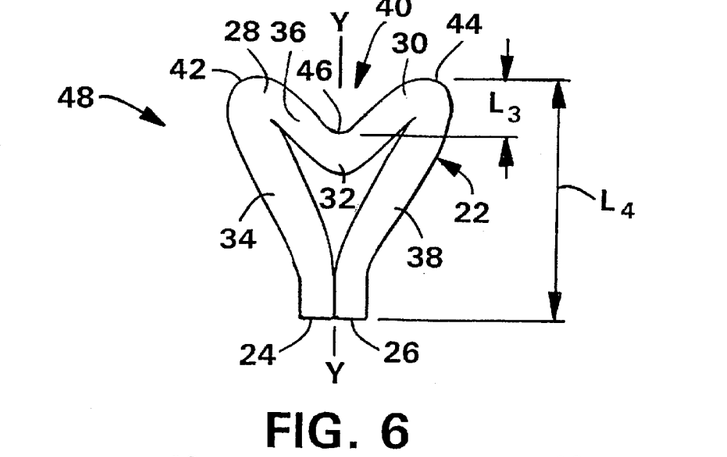
FIG. 6 is a side view of the softwind folded to form a generally M-shaped profile.

Referring to FIG. 6, the softwind 22 is folded or bent upon itself such that the first and second ends, 24 and 26 respectively, are aligned adjacent to one another and the softwind 22 contains three folds 28, 30 and 32 located between the ends 24 and 26. The three folds 28, 30 and 32 will form the softwind 22 into a generally M-shaped profile 48 with the first and second ends, 24 and 26 respectively, forming the base of the M-shaped profile 48. In this M-shaped profile 48, the softwind 22 is folded at 28 to form a first portion 34 and is folded at 30 to form a second portion 36 and a third portion 38. The first, second and third portions, 34, 36 and 38 respectively, can have approximately the same length. For example, if the softwind 22 has a length of about 6 inches (about 150 mm), each of the first, second and third portions 34, 36 and 38 respectively, can have a length of approximately two inches (about 50 mm). Alternatively, the first and third portions, 34 and 38 respectively, can have approximately the same length and the second portion 36 can be smaller or larger than either of the other two portions, 34 and 38 respectively. For example, if the softwind 22 has a length of about 6 inches (about 150 mm), the first and third portions, 34 and 38 respectively, can have a length of about 1.5 inches (about 37 mm) and the second portion 36 can have a length of about 3 inches (about 75 mm).

The softwind 22 is split along the vertically oriented Y—Y axis. The third fold 32 gives the softwind 22 the generally M-shaped profile 48 and also creates a cleft 40 which is spaced an equal distance between a first lobe 42 and a second lobe 44. The first and second lobes, 42 and 44 respectively, are created by the folds 28 and 30. The cleft 40 has a bottom surface or trough 46 which is aligned along the Y—Y axis. The depth of the cleft 40 has a dimension $L_3$ while the M-shaped profile 48 has an overall length $L_4$. The length $L_4$ is the vertical dimension of the M-shaped profile 48 measured along the Y—Y axis, between the tip of one of the lobes 42 or 44 and a line drawn through the base formed by the first and second ends 24 and 26. The length $L_3$ of the cleft 40 represents from between about 5% to about 80% of the length $L_4$, preferably, at least about 10% of the length of $L_4$, and most preferably, from between about 15% to about 50% of the length of $L_4$. It has been found that by forming the cleft 40 to a depth $L_3$, which falls between about 5% to about 80% of the total of the length $L_4$ of the M-shaped profile 48, that a tampon 62 can be formed which will span across the width of a woman's vaginal cavity.

Figure 7:
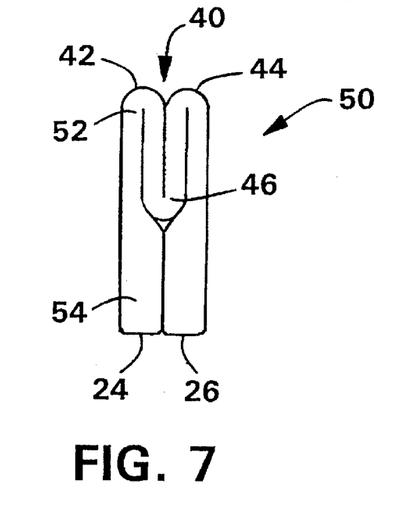
FIG. 7 is a side view of the softwind shown in FIG. 6 after it has been compressed into a pledget.

Referring to FIG. 7, a pledget 50 is shown which is formed by compressing the M-shaped profile 48 to a density of between about 0.1 grams per cubic centimeter (g/cc) to about 0.5 g/cc. Preferably, the M-shaped profile 48 is compressed to a density of from between about 0.15 g/cc to about 0.35 g/cc, and most preferably, to a density of about 0.25 g/cc. The M-shaped profile 48 is also heated from between about 200° F. to about 300° F. (about 93.3° C. to about 148.9° C.) for a time period of from between about 15 seconds to about 60 seconds. Preferably, the heat set occurs at about 240° F. (115.6° C.) and the time period is about 45 seconds.

The pledget 50 has an insertion end 52 and an opposite trailing end 54. The insertion end 52 will contain more absorbent material 10 than the trailing end 54 because of the folded configuration 28, 30 and 32 which occurs at the insertion end 52. However, when the pledget 50 is compressed into a generally cylindrical-shape, it will have an essentially constant exterior periphery and therefore the diameter of the insertion end 52 will be approximately equal to the diameter of the trailing end 54. The cleft 40 which is present at the insertion end 52 of the pledget 50 will be visibly present as a crease since the first and second lobes 42 and 44 will be brought into contact with one another when the pledget 50 is compressed.

Figure 8:
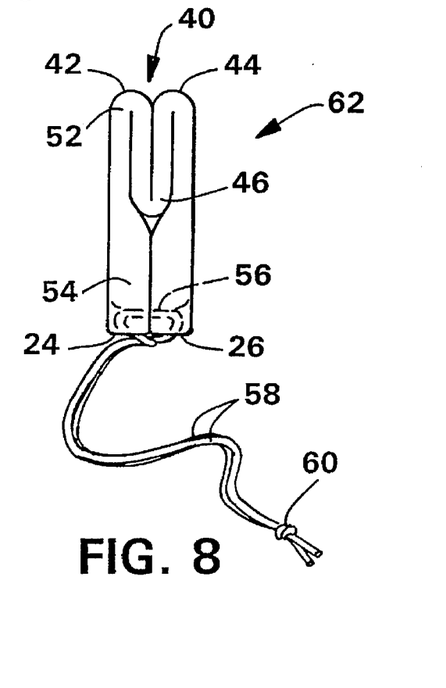
FIG. 8 is a side view of the pledget showing an aperture formed therethrough and a withdrawal string passing through the aperture and secured to the pledget.

Referring to FIG. 8, the compressed pledget 50 is then pierced by a sharp instrument to form an aperture 56. The aperture 56 should be formed in the trailing end 54 of the pledget 50 and should be situated close to the first and second ends, 24 and 26 respectively. The aperture 56 will pass through both the absorbent ribbon 10 and the cover 16. The aperture 56 can be formed by a sharp needle or awl once the pledget has been oriented relative to a carrier or jig such that the aperture 56 can be aligned perpendicular to the cleft 40. The importance of this orientation will be explained shortly.

A withdrawal string 58 is passed through the aperture 56 and looped upon itself so as to form a secure attachment to the pledget 50. The free ends of the withdrawal string 58 are tied into a knot 60 to assure that the withdrawal string 58 will not separate from the pledget 50. It should be noted that the withdrawal string 58 will serve to hold the first and second ends 24 and 26 of the pledget 50 in direct contact with one another. The withdrawal string 58 will also prevent the first and second ends 24 and 26 from expanding outward to any significant extent and certainly to a much lesser degree than is possible at the insertion end 52 of the pledget 50. Once the withdrawal string 58 is attached and secured to the pledget 50, a tampon 62 is formed.

The withdrawal string 58 can be constructed from various types of threads or ribbons. A thread or ribbon made from 100% cotton fibers works well. The withdrawal string 58 should have a length which extends beyond the trailing end 54 of the pledget 50 of from between about 2 inches to about 8 inches (about 50.8 mm to about 203.2 mm), preferably, from between about 4 inches to about 6 inches (about 102 mm to about 152.4 mm), and most preferably, about 5 inches (about 127 mm). The withdrawal string 58 can be dyed and/or treated with an anti-wicking agent, such as wax, before being secured to the pledget 50. The use of an anti-wicking agent will prevent any body fluids, such as menses or blood, from wicking along the withdrawal string 58 and contacting the inner surface of a woman's undergarment. A dry, clean withdrawal string 58 is preferred by the user, especially when she goes to remove the tampon 62 from her vagina.

Returning to FIG. 8, it should be noted that the insertion end 52 of the tampon 62 contains at least 1.25 times the amount of absorbent material 10 as does the trailing end 54. Preferably, the insertion end 52 will contain at least twice the amount of absorbent material 10 as the trailing end 54. This larger amount of absorbent material 10 at the insertion end 52 will cause the tampon 62 to asymmetrically expand during use such that the insertion end 52 will occupy a much larger area than the trailing end 54. It is important to note that the trailing end 54 will be prevented from significantly expanding by the attachment of the withdrawal string 58. This is important because the trailing end 54 will be the leading end upon removal of the tampon 62 from a woman's vagina. Because of this, it is advantageous to restrict the amount that the trailing end 54 can expand so as to make the withdrawal of the tampon 62 more comfortable to the user.

One will also notice that the M-shaped profile 48 allows the insertion end 52 to expand to a greater width dimension than thickness dimension. In this case, the width is shown as the distance between the first lobe 42 and the second lobe 44 while the thickness dimension goes into the paper, perpendicular to the vertical axis Y—Y. The reason for this is that the cross-section of a woman's vagina is not circular but instead is more rectangular in a relaxed state. More information on the geometry of a woman's vagina will be discussed below with reference to FIGS. 13–15.

Figure 9:
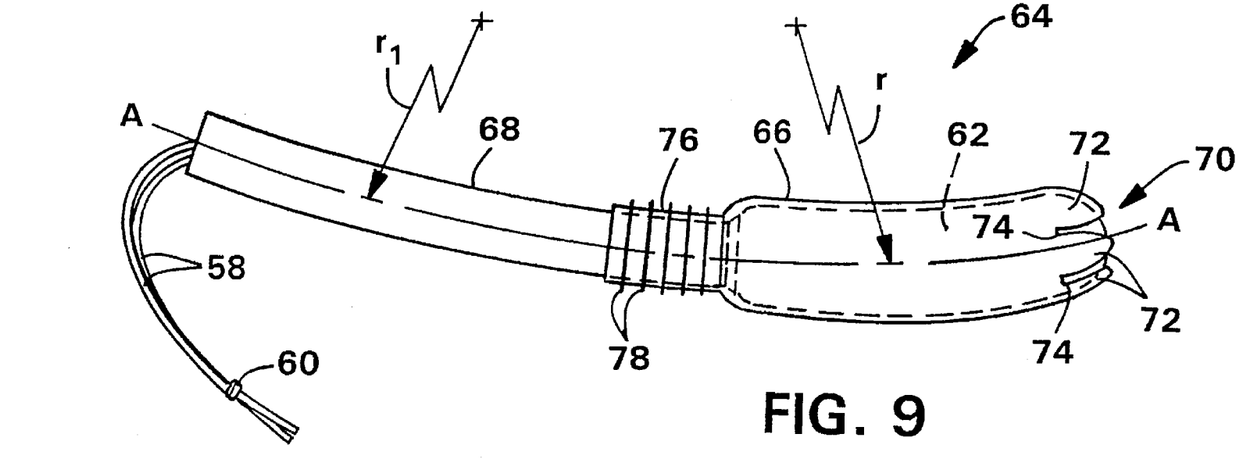
FIG. 9 is a side view of a two piece, arcuately shaped tampon applicator having an inner tube and an outer tube.
Figure 10:
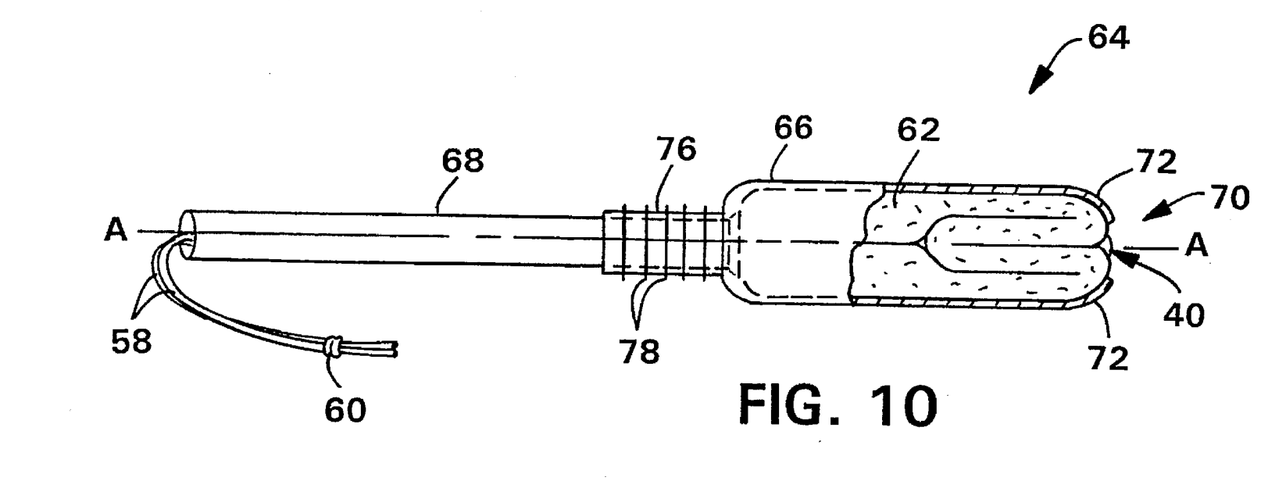
FIG. 10 is a cross-sectional view of the tampon applicator shown in FIG. 9, rotated 90° and partially broken away to show the orientation of the tampon relative to the curvature of the outer tube prior to insertion of the tampon into a woman's vagina.

Referring now to FIGS. 9 and 10, a tampon applicator 64 is shown having an arcuate or curved profile. The tampon applicator 64 includes an outer tube 66 and an inner tube 68. Preferably, both the outer tube 66 and the inner tube 68 are arcuate members formed on a radius and therefore each has an arcuate shape. It should be noted that the outer tube 66 has a radius "r" and the inner tube 68 has a radius "$r_1$", and the radius "r" can be equal to or different from the radius "$r_1$."

Both of the tubes 66 and 68 are hollow and each can be formed from similar or different materials. The materials can include paper, paperboard, cardboard, plastic, thermoplastic film, a combination thereof or any other type of suitable material. Preferably, both the outer tube 66 and the inner tube 68 are formed from the same material. The most common materials are paper, paperboard, cardboard and plastic. When paper or paperboard is used, it can be present as a single layer or as two or more layers. When two or more layers are used, they can be bonded together by an adhesive or glue to form a laminate structure. The outside surface of the outer tube 66 can also be coated with a wax or water-insoluble polymer to render it water-resistant.

Suitable plastic materials include polyolefins such as low density polyethylene and polypropylene. The outer tube 66 should have sufficient strength and rigidity to prevent collapsing under normal vaginal pressures. The outer tube 66 can be formed into a cylindrical shape having a longitudinal seam or be spirally or convolutely wound. The outer tube 66 has a relatively small diameter of from between about 10 mm to about 20 mm. The particular diameter of the outer tube 66 will depend upon the size of the tampon which is to be held therein. For example, a "junior" or "regular" size tampon will require a smaller diameter tube than would a "super" or a "super-plus" size tampon.

The inner tube 68 is slightly smaller in diameter than the outer tube 66 and is designed to telescopically slide within the inner diameter of the outer tube 66. Preferably, the inner tube 68 is made from the same material as the outer tube 66. It should be noted that the curved tampon applicator 64 could be constructed according to the teachings of Paul et al., U.S. Pat. No. 5,158,535 and assigned to Kimberly-Clark corporation. This patent is incorporated by reference and made a part hereof.

The tampon applicator 64 also contains an insertion tip 70 which is formed on one end of the outer tube 66 and contains a plurality of soft and flexible petals 72. The petals 72 can be arranged to form a dome-shaped nose. The petals 72 are separated by narrow slots 74. The slots 74 allow each petal 72 to radially flex or bend outward so as to provide an enlarged opening through which the tampon 62 can exit when it is pushed forward by the inner tube 68. Either an even or an odd number of petals 72 can be used, but preferably, there are an odd number of petals 72, such as 3, 5, 7, etc. By using an odd number of petals 72, one can prevent the outer tube 66 from collapsing or flattening after the tampon 62 has been expelled. Most preferably, the tampon applicator 64 will contain five petals 72. By preventing the outer tube 66 from collapsing, one can be assured that the vaginal tissue will not be pinched when the tampon applicator 64 is inserted or removed from the user's vagina. For optimum performance, all of the petals 72 should have approximately the same shape and dimension. Each of the petals 72 can have an elongated, approximately truncated shape, with a rounded end and each can have a length of about 7/16 of an inch (about 11.1 mm). The applicator 64 can also contain a fingergrip 76 formed on the opposite end of the outer tube 66. The fingergrip 76 can contain one or more ridges 78 which will prevent the user's fingers from slipping as she holds the tampon applicator 64. The fingergrip 76 can also contain flattened surfaces such as shown in U.S. Pat. No. 5,158,535, issued to Paul et al. The flattened surfaces are aligned perpendicular to the radius of curvature of the tampon applicator 64 such that it facilitates orientation of the applicator 64 into a woman's vagina.

It should also be noted that the tampon 62 will be oriented within the arcuately-shaped tampon applicator 64 such that the cleft 40 is aligned parallel with the radius "r" of the outer tube 66. That is, the cleft 40 is aligned perpendicular to the arcuately shaped centerline A—A shown FIG. 9. Another way of stating this is to say that in FIG. 10, the cleft 40 is aligned parallel to the arcuately-shaped centerline A—A since FIG. 10 is rotated 90° relative to FIG. 9 This alignment is important, for it will assure that the tampon 62 is correctly oriented within a woman's vagina after it is expelled from the tampon applicator 64.

Figure 11:
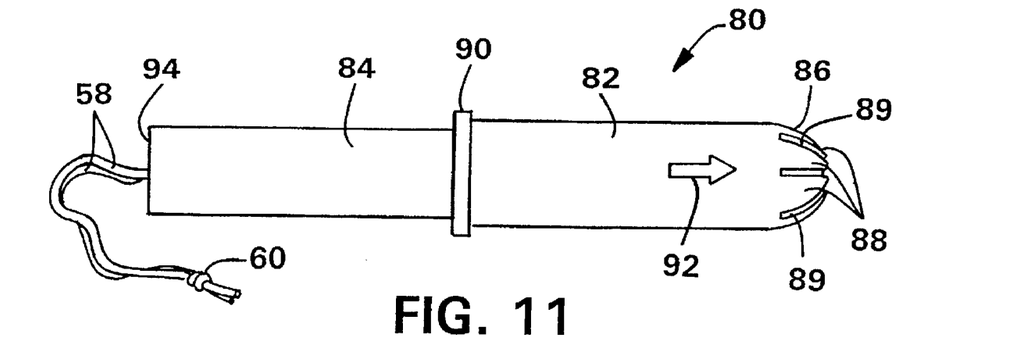
FIG. 11 is a side view of a two piece tampon applicator having an inner tube and an outer tube.
Figure 12:
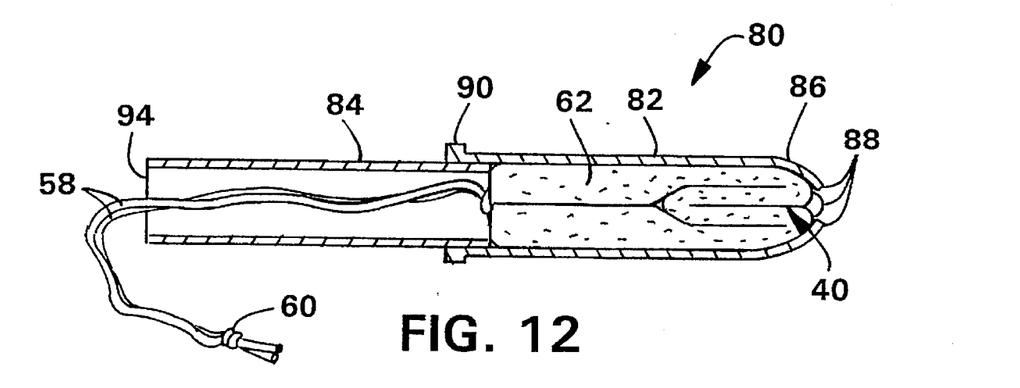
FIG. 12 is a cross-sectional view of the tampon applicator shown in FIG. 11 depicting the tampon being retained in the outer tube prior to insertion into a woman's vagina.

Referring now to FIGS. 11 and 12, a straight tampon applicator 80 is shown which is comprised of a hollow outer tube 82 and a hollow inner tube 84. The outer tube 82 is designed to house a tampon 62 while the inner tube 84 is telescopically slidable within the inner periphery of the outer tube 82 so as to expel the tampon 62 therefrom. The outer tube 82 has an insertion tip 86 which contains a plurality of petals 88 formed thereon. The petals 88 are separated by narrow slits or slots 89. The petals 88 and slots 89 serve the same function as the petals 72 and the slots 74 explained above in reference to FIGS. 9 and 10. The straight tampon applicator 80 also contains a fingergrip 90 in the form of a flange integrally formed on the opposite end of the outer tube 82. Since the straight tampon applicator 80 does not contain a curvature with which it can be oriented relative to a woman's vagina, it should contain some type of indicator 92 so as to aid the user in correctly orienting the tampon 62 relative to her vagina. The indicator 92 can be an arrow, a longitudinal line or some other type of marking which is painted, printed, embossed, applied or formed on the outer surface of the outer tube 82. For example, in FIG. 11, the indicator 92 is shown as an elongated arrow positioned adjacent to the insertion end 86. The tampon 62 should be inserted into the applicator 80 and oriented such that the cleft 40 is aligned parallel to the indicator 92.

It should also be noted that the inner tube 84 has a trailing end 94 which is spaced away from the fingergrip ring 90 when a tampon 62 is housed in the outer tube 82. As the inner tube 84 is pushed into the outer tube 82 to expel the tampon 62 therefrom, the trailing end 94 of the inner tube 84 will approach the fingergrip ring 90.

Figure 13:
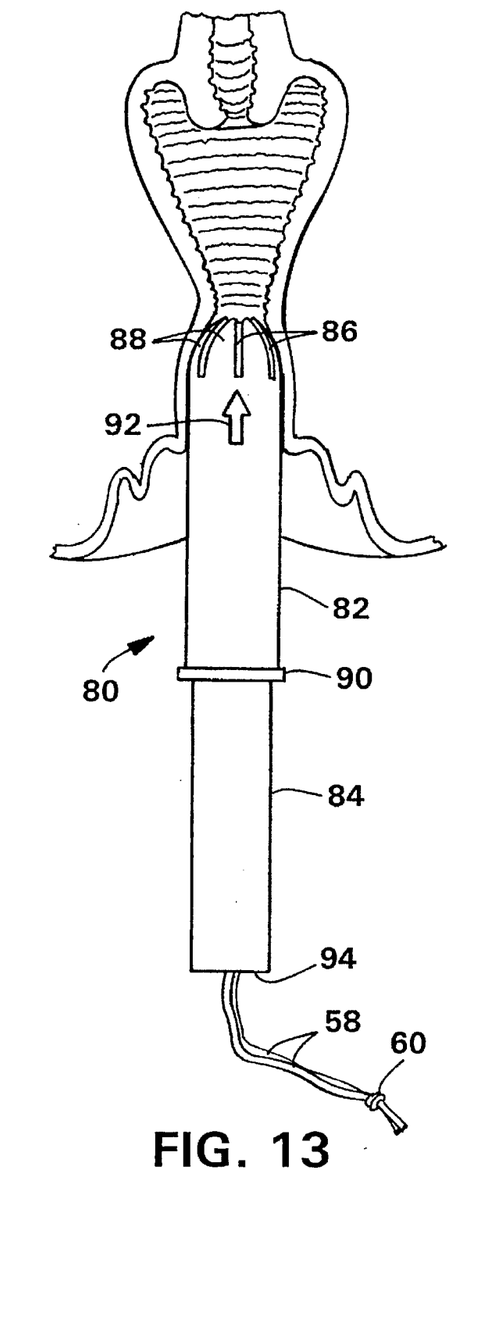
FIG. 13 is a front sectional view of a portion of the pelvic area of the female body taken in a plane through the cervix and introitus and showing the position of the tampon applicator immediately prior to expelling the tampon into the vagina.
Figure 14:
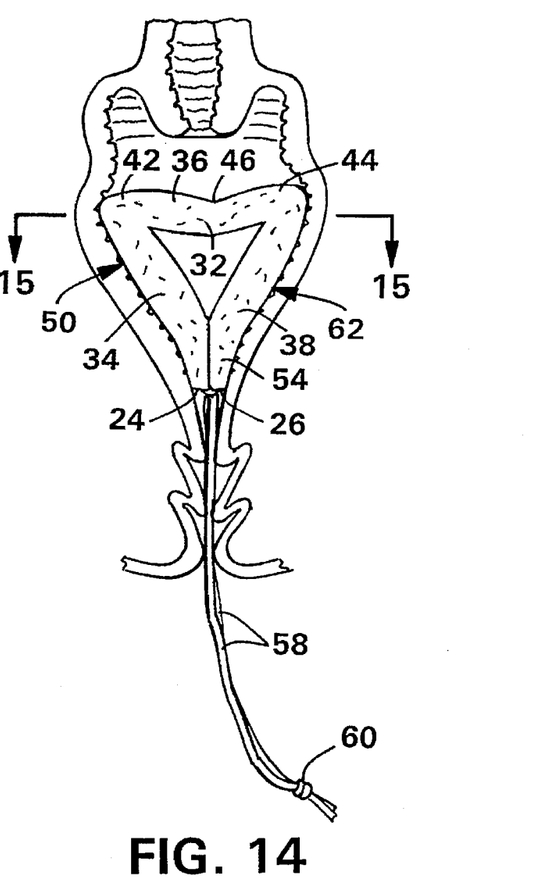
FIG. 14 is a view similar to that depicted in FIG. 13 showing the laterally expanded tampon after placement in the vagina and after the tampon applicator has been withdrawn.
Figure 15:
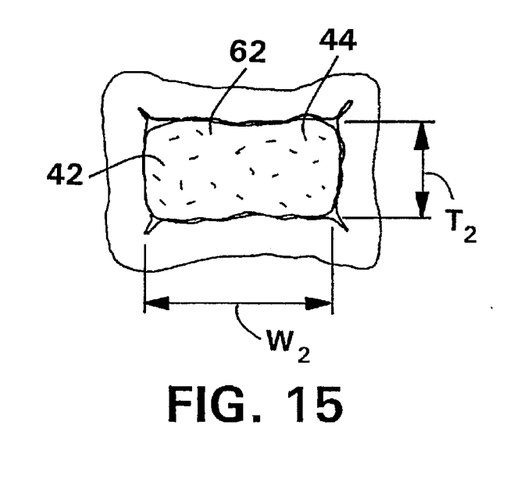
FIG. 15 is a vertical, lateral sectional view of the female vagina taken along line 15—15 of FIG. 14 illustrating how the laterally expandable tampon fills the cross-sectional area of the vagina.

Referring to FIGS. 13–15, the insertion and positioning of the tampon 62 within a woman's vagina will be described.

In FIG. 13, the straight tampon applicator 80 housing the tampon 62 is held by the user between her thumb and middle fingers. The thumb and middle fingers will contact the outer tube 82 just ahead of the fingergrip flange 90 while her index finger will rest on the trailing end 94 of the inner tube 84. The outer tube 82 is inserted through the introitus, until the insertion tip 86 is approximately in the lower end of the vagina. As the tampon applicator 80 is inserted, the indicator 92 should be aligned so that it is facing and parallel to the woman's belly button.

Once the outer tube 82 has been positioned such that the insertion tip 86 is adjacent to the lower end of the vagina, the user will push the inner tube 84 into the outer tube 82 with her index finger. As this occurs, the petals 88 will expand radially outward and allow the tampon 62 to be expelled into the vaginal cavity.

Referring to FIGS. 14 and 15, the orientation of the tampon 62 within the vaginal cavity is depicted. In FIG. 14, the tampon 62 is shown expanded laterally so that it occupies the opening of the vagina. In FIG. 15, the tampon 62 is shown having a width $W_2$ and a thickness $T_2$. The width $W_2$ is greater than the thickness $T_2$. Because of the unique shape of the vaginal cavity, in order to effectively prevent the leakage of body fluid from the vagina, a tampon must have a width $W_2$ to thickness $T_2$ ratio of greater than 1. Preferably, the width $W_2$ to thickness $T_2$ ratio is about 2:1.

The tampon 62 laterally expands to an open position, as that shown in FIG. 14, after being inserted into the vagina. The ability of the tampon 62 to expand to occupy the vagina cavity results from a number of phenomena, one being the natural resiliency of the compacted fibers within the tampon 62. A second factor is the folds 28, 30 and 32 which provide the absorbent 10 with a natural tendency to return to their non-compressed M-shaped profile 48. A third phenomenon is that the cover 16 which is folded along the absorbent 10 is aligned adjacent to itself in the area of the cleft 40. Since the cover 16 does not want to bond or adhere to itself, it has a natural tendency of spreading the absorbent 10 apart once the forces retaining the pledget 50 in a generally cylindrical shape are removed. In other words, once the pledget 50 is expelled from the outer tube 82, the absorbent 10 and cover 16 are free to expand outward to the M-shaped profile 48. The expansion of the second portion 36 of the tampon 62 allows a bridge to be formed across the vaginal cavity immediately below the cervix. This bridging effect causes the lobes 42 and 44 to move laterally outward and contact the inner walls of the vagina. This action essentially blocks the vaginal cavity and prevents the leakage of body fluid out of the vagina. While this is occurring, the trailing end 54 of the pledget 50 will stay together and expand to a much less extent in the width and thickness direction. This gives the tampon 62 an expanded configuration which best approximates the profile of the vagina, as shown in FIG. 13.

Tables One and Two present results of simulated use testing on tampons made according to the present invention, and several commercially available tampons. Table One shows that tampons made according to the present invention will expand to a wider width dimension than tampons commercially available. Table Two shows that tampons made according to the present invention also exhibit greater width expansion calculated as a percentage increase over the pre-use dimension.

Figure 16:
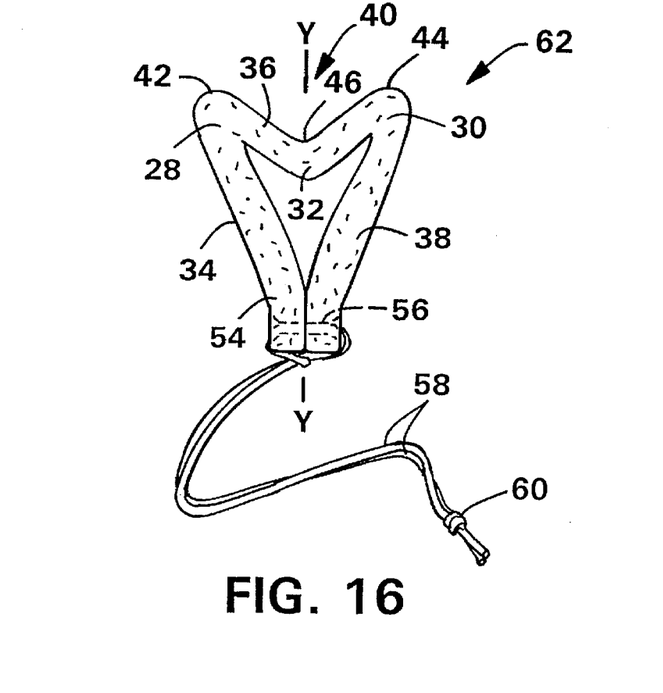
FIG. 16 is a side view showing one configuration of the laterally expandable tampon after removal from a woman's vagina.

Briefly, the simulated use testing was conducted as follows: After measuring each tampons initial maximum width (designated as Dry dimension in Table One) they were placed into a flexible tube contained within a hydraulic pressure chamber similar to that used for F.D.A. tampon absorbency testing. Pressure was increased to 0.26 PSI and ten milliliters of 0.9% saline fluid were applied to the tip of the tampon. One minute after the onset of leakage, tampons were removed from the chamber and again measured to determine their widest dimension (designated as Wet dimension in Table One). The test was repeated using five tampons of each type. The percentage increase shown in Table Two was calculated as follows:

lobes 42 and 44 will move closer together because of the presence of the third fold 32. The inner walls of the introital region will cause the lobes 42 and 44 to be pressed together as they exit the introital region. This particular M-shaped profile 48 permits for an easy and comfortable withdrawal of the tampon 62 from a woman's vagina.

TABLE ONE

TABLE TWO

A = M-shaped tampon prototype of this invention, regular absorbency
B = KOTEX® SECURITY tampons, regular absorbency
C = Playtex Ultimates, Unscented tampons, regular absorbency
D = Playtex Gentle Glide Applicator tampons, non-deodorant, regular absorbency
E = KOTEX® Curved tampons, regular absorbency
F = Tampax Plastic Applicator tampons, regular absorbency $$\frac{(\text{wet width} - \text{dry width})}{\text{dry width}} \times 100 = \text{percent increase in width}$$

In the expanded condition, the fold 32 may still be present such that the second portion 36 will be slightly less than horizontal. This arrangement means that the second portion will not be perpendicularly aligned to the introitus. The trough 46 of the cleft 40 will not rise up to the point where it is horizontally even with the lobes 42 and 44. This is important because it will facilitate withdrawal of the tampon 62 from the vaginal cavity.

Referring to FIG. 16, the general shape of the tampon 62 is shown as it is ready to be removed from the vaginal cavity. One will notice that the general M-shaped profile 48 is still present. As the trailing end 54 is moved downward into the introital region and out of the vagina, the introital region will expand. As one continues to withdraw the tampon 62, the

Method

Figure 17:
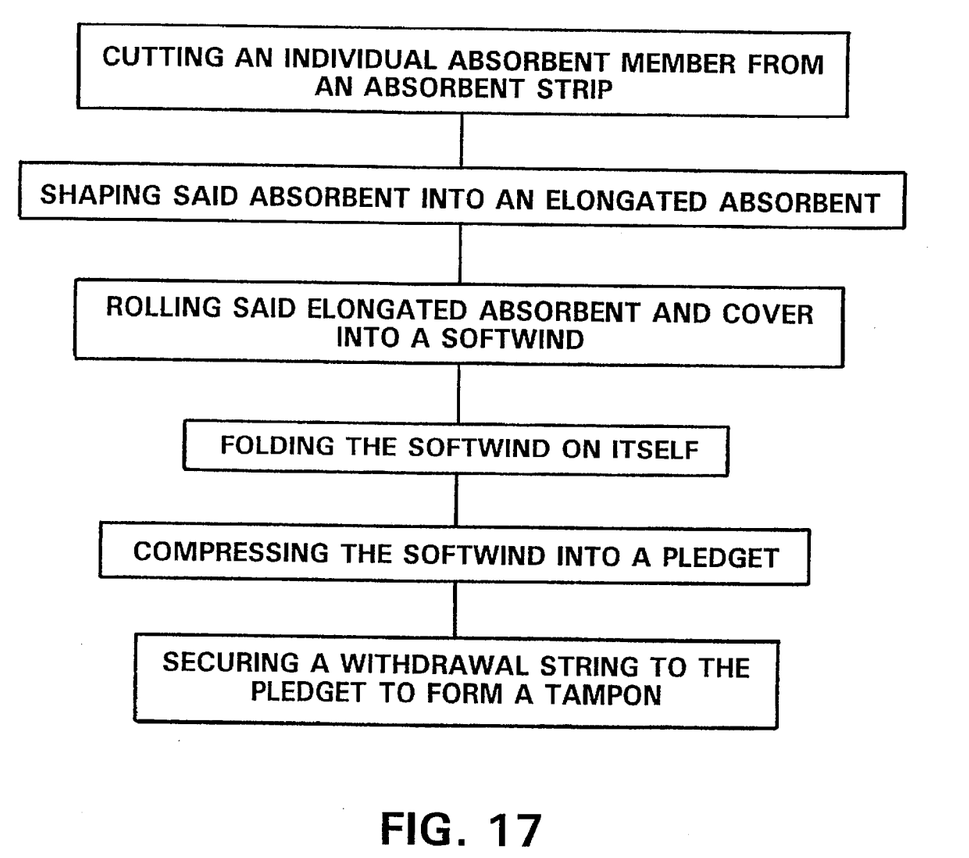
FIG. 17 is a flow diagram of a method of forming a laterally expandable tampon.

The method of forming the catamenial tampon 62 will now be explained with reference to the structure shown in FIGS. 1–12 and to the flow diagrams shown in FIGS. 17 and 18. The method includes cutting an individual absorbent member 12 from an absorbent strip 10. Each absorbent member 12 has a central longitudinal axis X—X and a central transverse axis Y—Y. The absorbent member 12 is then shaped to form an elongated absorbent 14 having an outer periphery 15. The absorbent member 12 can be shaped such as by rolling along the central transverse axis Y—Y or by folding the absorbent member 12 on its side or by a combination of folding and/or rolling the absorbent member 12 such as to form the elongated absorbent 14. A liquid permeable cover 16 is then secured to the outer periphery 15 of the elongated absorbent 14 to form a softwind 22. One specific example of securing the cover 16 to the elongated absorbent 14 is to place the elongated absorbent 14 on the liquid permeable cover 16 and then roll both the absorbent 14 and the cover 16 together to form the softwind 22. A depiction of this particular example is shown in FIG. 4.

The softwind 22 has a first end 24 and a second end 26. The two ends, 24 and 26 respectively, are spaced apart to a distance equal to the length $L_2$ of the softwind 22 when the softwind 22 is in a nonfolded condition. The softwind 22 is then folded on itself such that the first and second ends, 24 and 26 respectively, are aligned adjacent to one another. The softwind 22 should be folded such that it contains two folds 28 and 30, and preferably, three folds 28, 30 and 32. By folding the softwind 22 upon itself at least at folds, 28 and 30 respectively, a first portion 34, a second portion 36, and a third portion 38 are formed. The first, second, and third portions, 34, 36, and 38 respectively, can all be of the same length. Alternatively, the second portion 36 which bridges between the first portion 34 and the third portion 38 can be shorter in length than the first portion 34 and/or shorter in length than the third portion 38. Because the first and third portions, 34 and 38 respectively, establish the overall length of the pledget 50 which will be formed by shaping the softwind 22, it is advantageous to make both of them of the same length. When the softwind 22 is folded at least two times, the first and second ends, 24 and 26 respectively, will be aligned adjacent to one another so that they abut and end in a single plane. In other words, the outer surface of the first and second ends, 24 and 26 respectively, will be flush with one another. By folding the softwind 22 at least twice, and preferably three times, the softwind 22 will acquire a generally M-shaped profile 48. This M-shaped profile 48 is more pronounced when three folds 28, 30, and 32 are present.

Referring to FIG. 6, one will notice that the first portion 34 is approximately equal in length to the third portion 38, and that the second portion 36, in an extended position, will approximately equal the length of the first portion 34. When starting with a softwind 22 having a length of approximately 6 inches, it is advantageous to fold the softwind 22 at two locations 28 and 30. The two folds 28 and 30 are located between the first and second ends, 24 and 26 respectively, such that the second portion 36 will have a length of at least about 2 inches. When one starts with a softwind 22 greater than 6 inches, it is still advantageous to make the second portion 36 with a length of at least about 2 inches and to make the first and third portions, 34 and 38 respectively, of a slightly longer length.

As mentioned above, by folding the softwind 22 at three locations, 28, 30, and 32 respectively, all of which are located between the first and second ends, 24 and 26 respectively, the generally M-shaped profile 48 is readily obtained. In the M-shaped profile 48, a cleft 40 is established having a length or depth $L_3$. The length $L_3$ is the vertical distance measured from a horizontal line passing through the tips of the lobes 42 and 44 and a horizontal line passing tangentially through the bottom surface of the trough 46. This length $L_3$ will represent about 5 percent to about 80 percent of the length $L_4$ of the M-shaped profile 48.

The method further includes compressing the softwind 22, which has been folded into the M-shaped profile 48, into a pledget 50 having an insertion end 52 and a trailing end 54. One will notice that the insertion end 52 contains more absorbent than the trailing end 54. This occurs because of the folding of the softwind 22 such that additional absorbent material is present at the insertion end 52. After the pledget 50 has been formed, a withdrawal string 58 can be secured to the pledget 50 to form a tampon 62. In order to secure the withdrawal string 58 to the pledget 50, an aperture 56 is formed through the pledget 50 approximate the location of the trailing end 54. The trailing end 54 is established by the alignment of the first and second ends, 24 and 26 respectively. The withdrawal string 58 is then passed through the aperture 56 and looped upon itself. The two free ends are joined by a knot 60 to keep them together. The withdrawal string 58 will facilitate removal of the tampon 62 from a woman's vagina after it has accomplished its intended purpose. That is, after the tampon 62 has absorbed menstrual fluid, blood, and other body fluids normally discharged by a woman's vagina.

After the tampon 62 is formed, it can be positioned in a tampon applicator 64 or 80. The tampon applicator can be an arcuately-shaped applicator 64, as shown in FIGS. 9 and 10, or it can be a straight applicator 80, as shown in FIGS. 11 and 12. When the tampon 62 is positioned into the outer tube 66 of an arcuately-shaped tampon applicator 64, the cleft 40 has to be aligned parallel to the radius which forms the arcuately-shaped outer tube 66. This will assure that the tampon 62 is properly positioned within a woman's vagina after being expelled from the applicator 64. Likewise, when the tampon 62 is to be positioned in the outer tube 82 of a straight tampon applicator 80, the cleft 40 should be aligned parallel to the indicator 92. This will assure that the tampon 62 is properly positioned within a woman's vagina after being expelled from the applicator 80.

Figure 18:
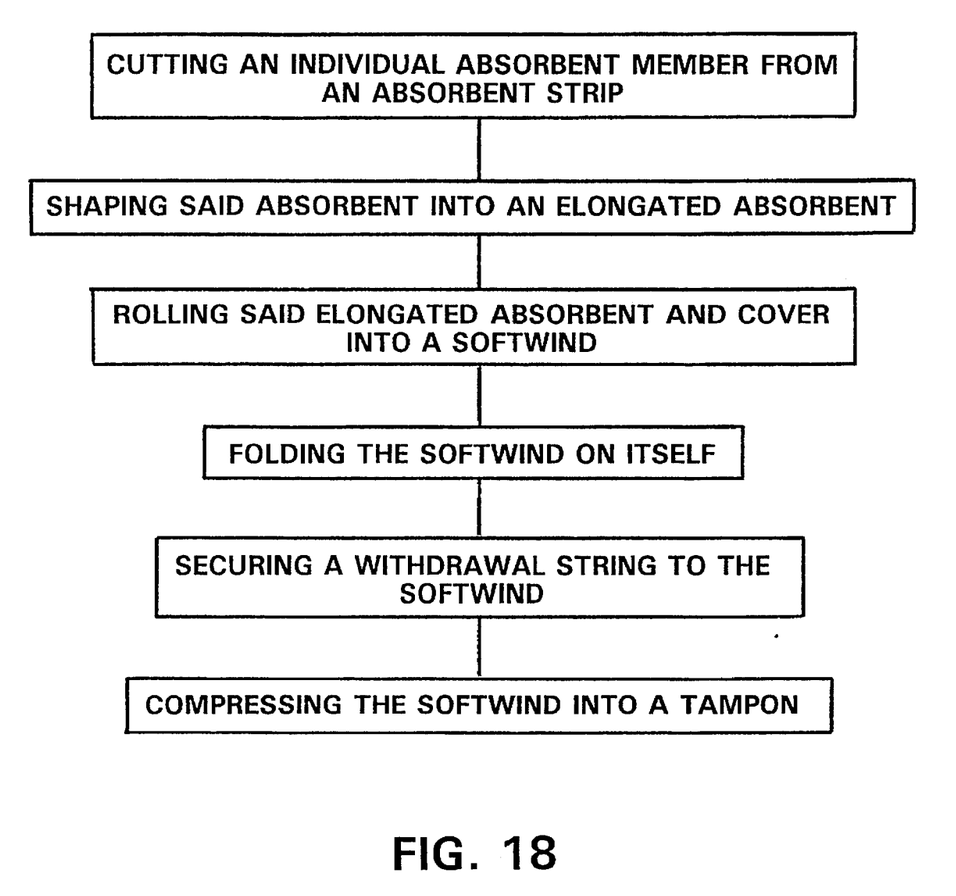
FIG. 18 is a flow diagram of an alternative method of forming a laterally expandable tampon.

An alternative method is depicted in the flow diagram of FIG. 18. In the alternative method, once the generally M-shaped profile 48 is formed, the withdrawal string 58 is secured to the softwind 22 approximate the location of the first and second ends, 24 and 26 respectively. After the withdrawal string 58 has been secured to the M-shaped profile 48, the softwind 22 is compressed into a tampon 62. The advantages of this alternative method versus the first method is that it may be easier to form the aperture 56 through the softwind 22 than through the compressed pledget 50.

It should be noted that after the withdrawal string 58 is passed through the aperture 56, that it is looped upon itself so that a secure attachment is obtained to the softwind 22 or to the pledget 50. The presence of the withdrawal string 58 securely attached to the trailing end 54 of the pledget 50 serves a very vital function. That is, the withdrawal string 58 will prevent the trailing end 54 of the pledget 50 from expanding to the same extent or degree as the insertion end 54 while in use. This is important because by restricting the amount the trailing end 54 can expand, one can facilitate a comfortable removal of the tampon 62 from the user's body. A comfortable removal of the tampon 62 is a required criteria for any type of tampon.

Lastly, the M-shaped profile 48 of the tampon 62 enables the insertion end 54 to contain more absorbent material than the trailing end 54. This additional absorbent material at the insertion end 52 is advantageous in intercepting fluid flow and preventing premature leakage of body fluid past the tampon 62. The M-shaped profile 48 also has the ability to expand to occupy the entire cross-sectional opening of the woman's vagina during use, and therefore is capable of preventing body fluid from leaking past the tampon 62.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A method of forming a tampon, said method comprising the steps of:
   a) cutting an individual absorbent member from an absorbent strip;
   b) shaping said absorbent member to form an elongated absorbent having an outer periphery;
   c) securing a liquid-permeable cover to said outer periphery of said elongated absorbent to form a softwind, said softwind having a first end and a second end;
   d) folding said softwind on itself such that said first and second ends are aligned adjacent to one another and said softwind contains two folds therebetween;
   e) compressing said softwind into a pledget; and
   f) securing a withdrawal string to said pledget to form a tampon, said withdrawal string facilitating removal of said tampon from a woman's vagina.

2. The method of claim 1 wherein said absorbent member has a central longitudinal axis and a central transverse axis; and said absorbent member is rolled along said central transverse axis to form said elongated absorbent.

3. The method of claim 1 wherein said pledget has an insertion end and a trailing end and said insertion end contains more absorbent than said trailing end.

4. The method of claim 1 wherein said two folds divide said softwind into a first portion, a second portion and a third portion.

5. The method of claim 4 wherein said second portion has a shorter length than said first portion.

6. The method of claim 4 wherein said first, second and third portions are of the same length.

7. The method of claim 4 wherein said second portion has a length of at least about 2 inches.

8. The method of claim 1 wherein said softwind contains three folds located between said first and second ends.

9. The method of claim 1 wherein said first and second ends of said softwind are held in contact with one another by said withdrawal string.

10. A method of forming a tampon, said method comprising the steps of:
    a) cutting an individual absorbent member from an absorbent strip, said absorbent member having a central longitudinal axis and a central transverse axis;
    b) rolling said absorbent member along said central transverse axis to form an elongated absorbent;
    c) placing said elongated absorbent on a liquid-permeable cover and rolling both said absorbent and said cover together to form a softwind, said softwind having a first end and a second end;
    d) folding said softwind on itself such that said first and second ends are aligned adjacent to one another and said softwind contains three folds therebetween, said softwind acquiring a generally M-shaped profile and having a cleft;
    e) compressing said softwind into a pledget having an insertion end and a trailing end, said insertion end containing more absorbent than said trailing end;
    f) securing a withdrawal string to said pledget to form a tampon, said withdrawal string facilitating removal of said tampon from a woman's vagina; and
    g) positioning said tampon into an arcuately-shaped outer tube formed on a radius with said cleft being aligned parallel with said radius.

11. A method of forming a tampon, said method comprising the steps of:
    a) cutting an individual absorbent member from an absorbent strip;
    b) shaping said absorbent member to form an elongated absorbent having an outer periphery;
    c) securing a liquid-permeable cover to said outer periphery of said elongated absorbent to form a softwind, said softwind having a first end and a second end;
    d) folding said softwind on itself such that said first and second ends are aligned adjacent to one another and said softwind contains two folds therebetween;
    e) securing a withdrawal string to said softwind; and
    f) compressing said softwind into a tampon.

12. The method of claim 11 wherein said absorbent member has a central longitudinal axis and a central transverse axis; and said absorbent member is rolled along said central transverse axis to form said elongated absorbent.

13. The method of claim 11 wherein said tampon is formed from a compressed pledget having an insertion end and a trailing end, and said insertion end containing more absorbent than said trailing end.

14. The method of claim 11 wherein said two folds divide said softwind into a first portion, a second portion and a third portion.

15. The method of claim 14 wherein said second portion has a shorter length than said first portion.

16. The method of claim 14 wherein said first, second and third portions are of the same length.

17. The method of claim 11 wherein said softwind contains three folds located between said first and second ends.

18. The method of claim 11 wherein said first and second ends of said softwind are held in contact with one another by said withdrawal string.

19. The method of claim 11 wherein an aperture is formed in said first and second ends of said softwind and said withdrawal string is passed through said aperture and looped upon itself to hold said withdrawal string secure thereto.

20. A method of forming a tampon, said method comprising the steps of:
    a) cutting an individual absorbent member from an absorbent strip, said absorbent member having a central longitudinal axis and a central transverse axis;
    b) rolling said absorbent member along said central transverse axis to form an elongated absorbent;
    c) placing said elongated absorbent on a liquid-permeable cover and rolling both said absorbent and said cover together to form a softwind, said softwind having a first end and a second end;
    d) folding said softwind on itself such that said first and second ends are aligned adjacent to one another and said softwind contains three folds therebetween, said softwind acquiring a generally M-shaped profile and having a cleft;
    e) securing a withdrawal string to said softwind;
    f) compressing said softwind into a tampon; and
    g) positioning said tampon into an arcuately-shaped outer tube formed on a radius with said cleft being aligned parallel with said radius.

* * * * *